United States Patent
Ko

(10) Patent No.: US 9,999,669 B1
(45) Date of Patent: *Jun. 19, 2018

(54) PHARMACEUTICAL COMPOSITION FOR INTESTINAL CANCER TREATMENT AND/OR PREVENTION

(71) Applicant: Feng Chia University, Taichung (TW)

(72) Inventor: Tse-Hao Ko, Taichung (TW)

(73) Assignee: FENG CHIA UNIVERSITY, Taichung (TW)

(*) Notice: Subject to any disclaimer, the term of this patent is extended or adjusted under 35 U.S.C. 154(b) by 0 days. days.

This patent is subject to a terminal disclaimer.

(21) Appl. No.: 15/705,871

(22) Filed: Sep. 15, 2017

(30) Foreign Application Priority Data

Aug. 17, 2017 (TW) .............. 106127979 A

(51) Int. Cl.
*A61K 47/02* (2006.01)
*A61K 33/38* (2006.01)
*A61K 33/34* (2006.01)

(52) U.S. Cl.
CPC .............. *A61K 47/02* (2013.01); *A61K 33/34* (2013.01); *A61K 33/38* (2013.01)

(58) Field of Classification Search
CPC ......... A61K 47/02; A61K 33/38; A61K 33/34
See application file for complete search history.

(56) References Cited

U.S. PATENT DOCUMENTS 9,358,254 B2 * 6/2016 Ko .................. A61K 33/38

* cited by examiner

*Primary Examiner* — Trevor Love
(74) *Attorney, Agent, or Firm* — Muncy, Geissler, Olds & Lowe, P.C.

(57) ABSTRACT

A method for treatment and/or prevention of intestinal cancer is provided, and the method includes: administering a composition to a subject in need thereof, the composition comprising a carbonaceous material and an active particle positioned on the carbonaceous material and made of silver, gold, zinc, copper, magnesium, selenium, platinum, arsenic, cobalt, calcium, silicon, and any combination thereof.

12 Claims, 5 Drawing Sheets

PHARMACEUTICAL COMPOSITION FOR INTESTINAL CANCER TREATMENT AND/OR PREVENTION

CROSS REFERENCE

The non-provisional application claims priority from Taiwan Patent Application NO. 106127979, filed on Aug. 17, 2017, the content thereof is incorporated by reference herein.

FIELD OF THE INVENTION

The present invention is directed to a pharmaceutical composition, and particularly to a pharmaceutical composition for intestinal cancer treatment and/or prevention.

BACKGROUND OF THE INVENTION

According to the World Health Organization, intestinal cancer is the second most common cancer in women and the third most common cancer in men worldwide in 2012. Intestinal cancer is also the fourth leading cause of death from cancer worldwide in 2012 after lung cancer, gastric cancer, and liver cancer. Treatments for intestinal cancer include surgery, radiation therapy, chemotherapy, or targeted therapy. However, the high morality of intestinal cancer reveals that the treatment efficacy is not as expected.

Accordingly, there is a need to develop a novel pharmaceutical composition for intestinal cancer treatment.

SUMMARY OF THE INVENTION

An objective of the present invention is to provide a method for treatment and/or prevention of intestinal cancer, and the method includes: administering a composition to a subject in need thereof, the composition comprising a carbonaceous material and an active particle positioned on the carbonaceous material and made of silver, gold, zinc, copper, magnesium, selenium, platinum, arsenic, cobalt, calcium, silicon, or any combination thereof.

DETAILED DESCRIPTION OF THE INVENTION

Figure 1:
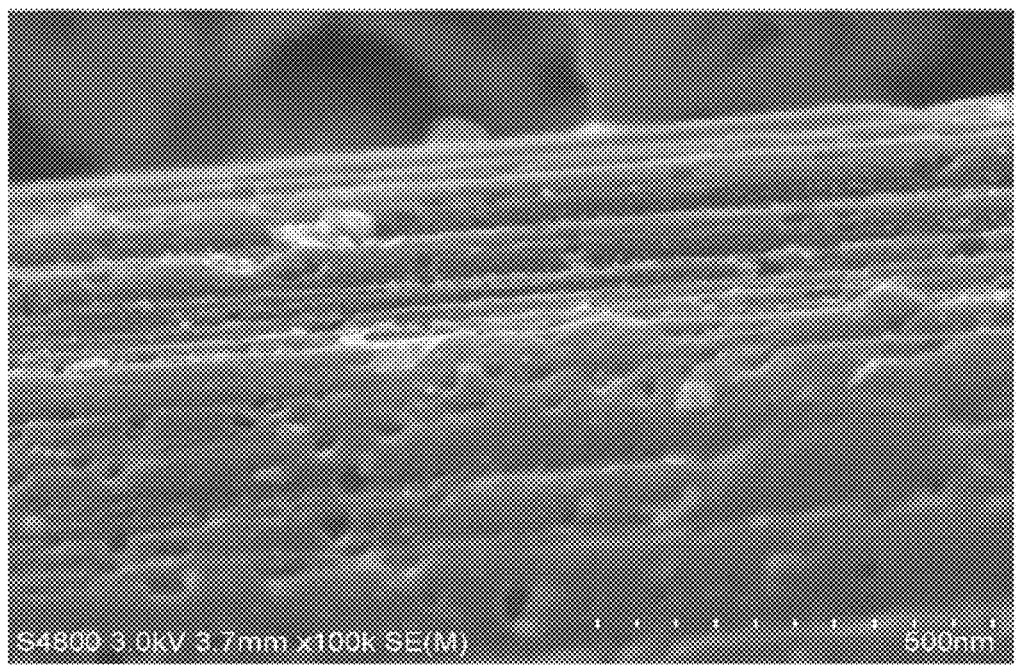
FIG. 1 is a scanning electron microscopy (SEM) picture showing a composition obtained in Example 1.
Figure 2:
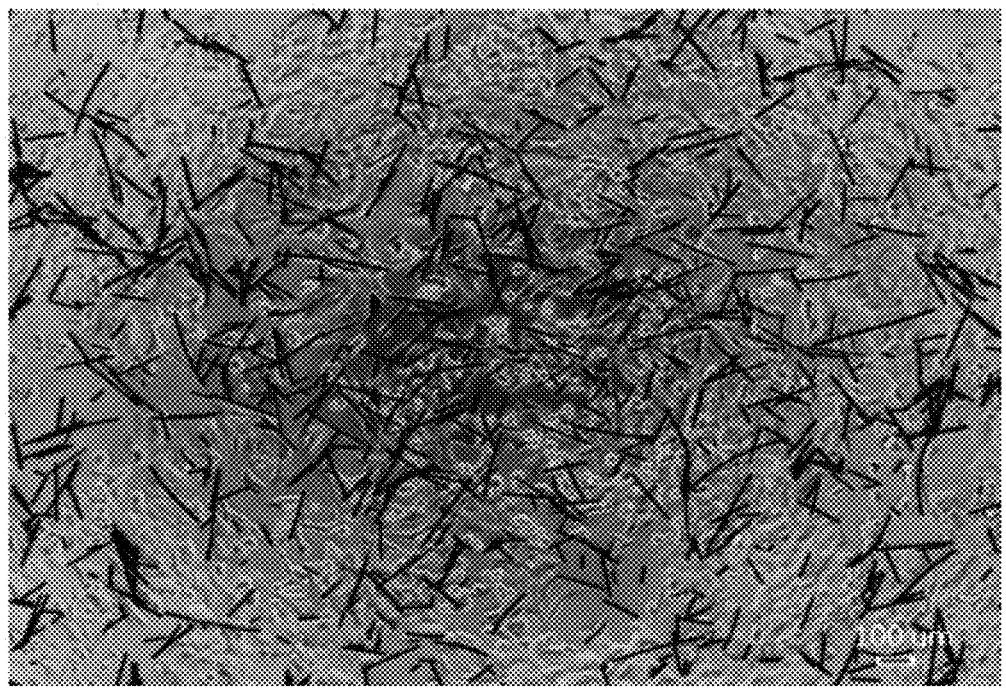
FIG. 2 is an optical microscopy picture showing HCT-116 human colon cancer cells treated with a composition obtained in Example 1 in 0.1 mg/mL for 24 hours.
Figure 3:
FIG. 3 is an optical microscopy picture showing Caco-2 human colon cancer cells treated with a composition obtained in Example 1 in 0.1 mg/mL for 24 hours.
Figure 4:
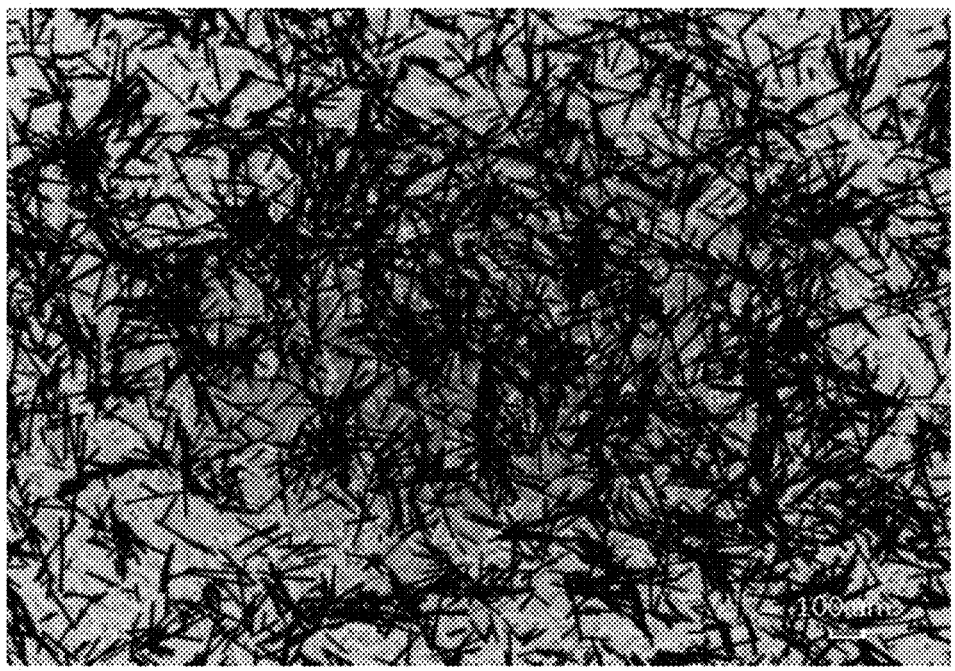
FIG. 4 is an optical microscopy picture showing HCT-116 human colon cancer cells treated with a composition obtained in Example 1 in 0.5 mg/mL for 24 hours.
Figure 5:
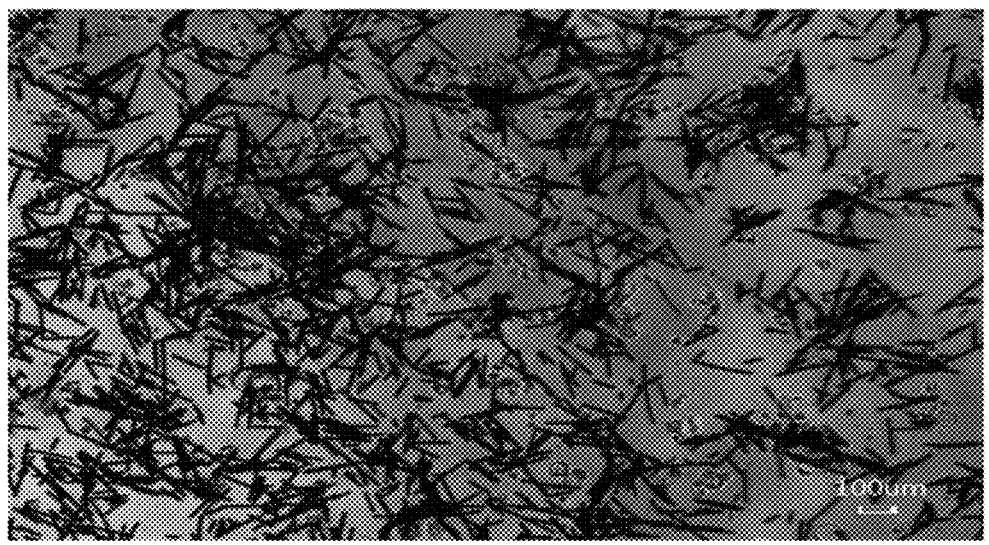
FIG. 5 is an optical microscopy picture showing Caco-2 human colon cancer cells treated with a composition obtained in Example 1 in 0.5 mg/mL for 24 hours.

The detailed description and preferred embodiments of the invention will be set forth in the following content, and provided for people skilled in the art so as to understand the characteristics of the invention.

An embodiment of the present invention discloses a method for treatment and/or prevention of intestinal cancer, and the method comprises: administering a composition to a subject in need of this treatment and/or this prevention. The composition comprises a carbonaceous material and an active particle, and the active particle is positioned on the carbonaceous material and made of silver, gold, zinc, copper, magnesium, selenium, platinum, arsenic, cobalt, calcium, silicon, or any combination thereof. After the administration of the composition to the subject, the carbonaceous material can absorb the intestinal cancer cells or attach to the intestinal cancer tissues. Since the intestinal cancer cells are highly negatively charged on their surfaces, cations released from the active particle can attach to the cell surfaces to destroy cell membranes. By such a manner, the growth of intestinal cancer cells can be inhibited.

The term "treatment" used in the content indicates the purpose to diminish, retard, or stop the growth, metastasis, or spread of intestinal cancer cells; the term "prevention" used in the content indicates the purpose to avoid the growth, metastasis, or spread of intestinal cancer cells; the term "intestinal cancer" used in the content indicates colon cancer, rectal cancer, or colorectal cancer. Furthermore, an example of the carbonaceous material is, but not limited to, an activated carbon fiber, an activated carbon powder, a charcoal material, a bamboo charcoal granule, a carbon black, a graphite powder, an expanded graphite powder, a graphene, a nano carbon powder, or a carbon powder made from phenol formaldehyde resins or artificial resins. Based on the total weight of the composition, the carbonaceous material may be present in 80 wt %-99.9999 wt %, and the active particle may be present in 0.0001 wt %-20 wt %. In the embodiment, a BET surface area of the carbonaceous material may be of 0.1-2,500 $m^2/g$, and preferably of 600-1,800 $m^2/g$. In the embodiment, the active particle size may be of 1 nm-200 μm, and preferably of 5 nm-100 μm.

According to the examples below, the composition may be administered to the subject in 0.01-30 g/kg of the subject's body weight per day, preferably in 0.01-24 g/kg of the subject's body weight per day, more preferably in 0.01-1 g/kg of the subject's body weight per day, and even more preferably in 0.1-0.5 g/kg of the subject's body weight per day. In addition, the composition can be orally or intratumorally administered to the subject, and formulated in various dosage forms, e.g. a capsule, a tablet, a powder, a suspension, or an emulsion. For the formulation in various dosage forms, the composition may further comprise an additive, such as a nutrient (vitamin), a flavoring agent (citric acid, malic acid, acetic acid, or lactic acid), a sweetening agent (glucose, oligosaccharide, fructose, maltose, aspartame, saccharin, sucralose, acesulfame potassium, glycyrol, stevioside, glycyrrhizin, sorbitol, maltitol, or xylitol), a pasting agent (wheat starch, egg white, curdlan, carboxymethyl cellulose, sodium alginate, curdlan, sodium carboxymethylcellulose, acidified starch, gelatinized starch, bleached starch, oxidized starch, starch acetate, or starch phosphate), a solvent (propanediol or glycerol), an emulsifying agent (fatty acid glyceride), or a moisture-controlling agent (sorbitol, lactic acid, glycerol, or propanediol).

For enhancing the intestinal cancer cell absorption efficacy, the carbonaceous material may further have a pore. Generally, the carbonaceous material can absorb not only the intestinal cancer cells, but also normal cells (non-cancer cells) or beneficial substances such as vitamins, enzymes, or probiotics. For avoiding the normal cell or beneficial substance absorption, the pore radius may be of more than 0 nm but less than 2.5 nm (0 nm<pore radius<2.5 nm), and preferably of 0.5 nm-2.3 nm. For ease of the administration, on condition that the carbonaceous material is in the form of a granule, its granule size may be of more than 1 nm but less than 3 nm (1 nm<granule size<3 nm); on condition that the carbonaceous material is in the form of a bar, its length may be of more than 1 nm but less than 3 nm (1 nm<length<3 nm), and its cross-sectional diameter may be of more than 1 nm but less than 3 nm (1 nm<cross-sectional diameter<3 nm); on condition that the carbonaceous material is in the form of an irregular, the maximum length may be of more than 1 nm but less than 3 nm (1 nm<maximum length<3 nm). For providing the composition with various hydrophilicities, the carbonaceous material may further have various acidic groups or various basic groups, and the total acidic group content or the total basic group content may be of above 0.3 mEq/g.

The manufacture method of the composition used in the embodiment is disclosed below:

First of all, an active solution containing an active salt is provided. The active salt is used as the source of the later obtained active particle, and its concentration may be of 0.00001 M-20 M. An example of the active salt is, but not limited to, a silver salt, a gold salt, a zinc salt, a copper salt, a magnesium salt, a selenium salt, a platinum salt, an arsenic salt, a cobalt salt, a calcium salt, or a silicon salt. For example, the active salt is a metal halide (e.g. silver fluoride, silver chloride, silver bromide, or silver iodide), a metal acetate (e.g. silver acetate), a metal nitrate (e.g. silver nitrate, copper nitrate, or zinc nitrate), a metal phosphate (e.g. silver phosphate), or a metal sulfonate (e.g. silver sulfonate). For uniform distribution of the later obtained active particle on the carbonaceous material, the active solution may further contain a reductant, and an example thereof is, but not limited to, glacial acetic acid, ammonia water, ascorbic acid, or glucose.

Next, the carbonaceous material is immersed in the active solution or the active solution is sprayed onto the carbonaceous material. During the immersing, the carbonaceous material may be soaked in the active solution under a stir for 0.5-24 hours, and preferably for 1-12 hours. Based on the sum weight of the carbonaceous material and the active solution, the active salt may be present in 0.01 wt %-1 wt %, and the carbonaceous material may be present in 0.01 wt %-20 wt %. On condition that the solution contains the reductant, based on the sum weight of the carbonaceous material and the active solution, the active salt may be present in 0.01 wt %-1 wt %, the carbonaceous material may be present in 0.01 wt %-20 wt %, and the reductant may be present in 0.01 wt %-30 wt %.

Afterward, the active solution is thermally dried so that the active salt is attached to the carbonaceous material. During the thermally drying, the active solution is stayed at 80-500° C. for 0.5-10 hours, and preferably for 1-4 hours.

Then, the active salt is pyrolyzed to convert into the active particle so that the composition is obtained. During the pyrolyzing, the active salt is stayed at 200-1000° C. for 0.5-10 hours. Additionally, the pyrolyzing step may be performed in the presence of a nitrogen gas, in the presence of an inert gas, or under a vacuum.

Subsequently, the composition is washed with water to remove any dissociated particle. During the washing, the composition may be soaked in the water or rinsed with the water for 0.5-6 hours.

Finally, the composition is thermally dried to remove any remaining liquid. During the thermally drying herein, the composition may be stayed at 80-120° C. for 0.5-6 hours.

The following examples are offered to further illustrate the present invention:

Example 1

A polyacrylonitrile (PAN)-based activated carbon fiber fabric was provided, which had a BET specific surface area of 1,100 $m^2/g$ and a carbon content of 80.7 wt %. After being soaked in a 0.0025 M silver nitrate aqueous solution for 2 hours, the fiber fabric was thermally dried at 100° C. for 2 hours so that the silver nitrate was attached to the fiber fabric. The silver nitrate was then pyrolyzed at 600° C. and in the presence of a nitrogen gas for 1.5 hours so as to convert into a silver particle attached to the fiber fabric. Hereafter, the fiber fabric was washed with water for 2 hours to remove any dissociated particle. After which, the fiber fabric and the silver particle attached thereto were thermally dried to remove any liquid. Finally, the fiber fabric was ground so as to form a composition (FIG. 1), and the composition had the silver particle and an activated carbon fiber powder carrying the silver particle. The composition had the following characteristics: a carbon content of 78.1 wt %, a silver content of 0.3 wt %, a length of less than 0.1 mm, a BET specific surface area of 980 $m^2/g$, a pore radius of the powder of 2.41 nm, and a particle size of less than 100 nm.

Example 2

A polyacrylonitrile (PAN)-based activated carbon fiber fabric was provided, which had a BET specific surface area of 1,100 $m^2/g$ and a carbon content of 80.7 wt %. After being soaked in a 0.0025 M silver nitrate and 0.0025 M copper nitrate aqueous solution for 2 hours, the fiber fabric was thermally dried at 100° C. for 2 hours so that the silver nitrate and the copper nitrate were attached to the fiber fabric. The silver nitrate and the copper nitrate were pyrolyzed at 600° C. and in the presence of a nitrogen gas for 1.5 hours so as to convert into a silver particle and a copper particle both attached to the fiber fabric. Hereafter, the fiber fabric was washed with water for 2 hours to remove any dissociated particle. After which, the fiber fabric and each particle attached thereto were thermally dried to remove any liquid. Finally, the fiber fabric was ground so as to form a composition, and the composition had the silver particle, the copper particle, and an activated carbon fiber powder carrying the both particles. The composition had the following characteristics: a carbon content of 78.0 wt %, a silver content of 0.32 wt %, a copper content of 0.30 wt %, a length of less than 0.1 mm, a BET specific surface area of 980 $m^2/g$, a pore radius of the powder of 2.41 nm, a silver particle size of less than 100 nm, and a copper particle size of less than 200 nm.

Analysis 1

According to the International Organization for Standardization (ISO) 10993-5: 2009 (E) standard, L929 mouse fibroblasts were incubated with each composition obtained in the above Examples for 24 hours so as to perform cytotoxicity analysis. The amount of each composition used herein was of 24 mg/mL of the sum volume of the cells and the cell culture media. As shown in Table 1, each composition exhibits no toxicity to normal cells in a high amount.

TABLE 1

Cytotoxicity of each composition

| | Ratio of rounded or cracked cells (%) |
|---|---|
| Example 1 | 29 |
| Example 2 | 30 |

Analysis 2

HCT-116 human colon cancer cells, Caco-2 human colon cancer, SW-48 human colon cancer cells, or HT-29 human colorectal cancer cells were incubated with the composition obtained in Example 1 for 24 hours so as to perform MTT (3-(4,5-Dimethylthiazol-2-yl)-2,5-diphenyltetrazolium bromide) assay. The amounts used herein were shown in Table 2, and each indicated the weight of the composition in 1 mL of the sum volume of the cells and the cell culture media. As shown in FIGS. 2-5 and Table 2, the composition obtained in Example 1 exhibits toxicity to human intestinal cancer cells in a low amount. It can be expected that the composition obtained in Example 1 still exhibits toxicity to human intestinal cancer cells in a high amount.

TABLE 2

Cytotoxicity of the composition in various amounts

| Amount | Inhibition rate (%) | | | |
|---|---|---|---|---|
| (mg/mL) | HCT-116 | Caco-2 | SW-480 | HT-29 |
| 0 | 0 | 0 | 0 | 0 |
| 0.1 | 18 ± 6 | 40 ± 5 | 6 ± 7 | 14 ± 2 |
| 0.5 | 46 ± 4 | 76 ± 3 | 85 ± 2 | 59 ± 11 |
| 1.0 | 79 ± 3 | 86 ± 4 | 95 ± 1 | 79 ± 5 |

As described above, the composition of the embodiment indeed has a high potential to be used as a pharmaceutical composition for intestinal cancer treatment and/or prevention.

While the invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A method for treatment of intestinal cancer, comprising:
   administering orally or intratumorally a composition to a subject in need thereof, the composition comprising:
   a carbonaceous material; and
   an active particle positioned on the carbonaceous material and made of silver, gold, zinc, copper, magnesium, selenium, platinum, arsenic, cobalt, calcium, silicon, or any combination thereof,
   wherein the carbonaceous material has an acidic group or a basic group, and
   wherein the composition is administered to the subject in 0.01-1 g/kg of the subject's body weight per day.

2. The method as claimed in claim 1, wherein the intestinal cancer is colon cancer, rectal cancer, or colorectal cancer.

3. The method as claimed in claim 1, wherein the carbonaceous material is an activated carbon fiber, an activated carbon powder, a charcoal material, a bamboo charcoal granule, a carbon black, a graphite powder, an expanded graphite powder, a graphene, a nano carbon powder, or a carbon powder made from phenol formaldehyde resins or artificial resins.

4. The method as claimed in claim 1, wherein based on total weight of the composition, the carbonaceous material is present in 80 wt %-99.9999 wt %, and the active particle is present in 0.0001 wt %-20 wt %.

5. The method as claimed in claim 1, wherein a BET surface area of the carbonaceous material is of 0.1-2,500 $m^2/g$.

6. The method as claimed in claim 1, wherein a particle size of the active particle is of 1 nm-200 µm.

7. The method as claimed in claim 1, wherein the composition is administered to the subject in 0.1-0.5 g/kg of the subject's body weight per day.

8. The method as claimed in claim 1, wherein the composition is administered to the subject in 0.5-1 g/kg of the subject's body weight per day.

9. The method as claimed in claim 1, wherein the composition further comprises an additive.

10. The method as claimed in claim 1, wherein the carbonaceous material has a pore.

11. The method as claimed in claim 10, wherein a radius of the pore is of more than 0 nm but less than 2.5 nm.

12. The method as claimed in claim 1, wherein on condition that the carbonaceous material is in the form of a granule, a granule size of the carbonaceous material is of more than 1 nm but less than 3 nm; on condition that the carbonaceous material is in the form of a bar, a bar length of the carbonaceous material is of more than 1 nm but less than 3 nm, and a cross-sectional diameter of the carbonaceous material is of more than 1 nm but less than 3 nm; or on condition that the carbonaceous material is in the form of an irregular, a maximum length of the carbonaceous material is of more than 1 nm but less than 3 nm.

* * * * *